(12) United States Patent
Hershey

(10) Patent No.: US 9,694,184 B2
(45) Date of Patent: *Jul. 4, 2017

(54) HIGH FREQUENCY NEUROMODULATION SYSTEM AND METHOD FOR REDUCING ENERGY REQUIREMENTS

(71) Applicant: Boston Scientific Neuromodulation Corporation, Valencia, CA (US)

(72) Inventor: Bradley Lawrence Hershey, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/191,278

(22) Filed: Jun. 23, 2016

(65) Prior Publication Data

US 2016/0303380 A1  Oct. 20, 2016

Related U.S. Application Data

(63) Continuation of application No. 13/930,493, filed on Jun. 28, 2013, now Pat. No. 9,403,015.

(Continued)

(51) Int. Cl.
*A61N 1/36* (2006.01)
*A61N 1/39* (2006.01)
(Continued)

(52) U.S. Cl.
CPC ....... *A61N 1/36196* (2013.01); *A61N 1/0551* (2013.01); *A61N 1/0556* (2013.01);
(Continued)

(58) Field of Classification Search
CPC ............ A61N 1/36171; A61N 1/36128; A61N 1/36132; A61N 1/36135; A61N 1/36185; A61N 1/36196

See application file for complete search history.

(56) References Cited

U.S. PATENT DOCUMENTS 6,516,227 B1  2/2003  Meadows et al.
6,895,280 B2  5/2005  Meadows et al.
(Continued)

FOREIGN PATENT DOCUMENTS

WO  WO-2006044793 A2  4/2006
WO  WO-2014005024 A1  1/2014

OTHER PUBLICATIONS

"U.S. Appl. No. 13/930,493, Advisory Action mailed Jun. 3, 2015", 5 pgs.
(Continued)

*Primary Examiner* — Joseph Dietrich
(74) *Attorney, Agent, or Firm* — Schwegman Lundberg & Woessner, P.A.

(57) ABSTRACT

An electrical neuromodulation system and method of treating an ailment of a patient using a neuromodulation device. Electrical modulation energy is delivered at a first frequency from the neuromodulation device to a first set of electrodes having a first combined electrode impedance. A second set of electrodes having a second combined electrode impedance less than the first combined electrode impedance is automatically selected. The electrical modulation energy is delivered at a second frequency to the second set of electrodes, wherein the second frequency is greater than the first frequency.

20 Claims, 9 Drawing Sheets

Related U.S. Application Data

(60) Provisional application No. 61/666,568, filed on Jun. 29, 2012.

(51) Int. Cl.
*A61N 1/362* (2006.01)
*A61N 1/05* (2006.01)

(52) U.S. Cl.
CPC ......... *A61N 1/362* (2013.01); *A61N 1/36003* (2013.01); *A61N 1/3605* (2013.01); *A61N 1/36007* (2013.01); *A61N 1/36071* (2013.01); *A61N 1/36075* (2013.01); *A61N 1/36171* (2013.01); *A61N 1/36185* (2013.01); *A61N 1/3956* (2013.01); *A61N 1/3606* (2013.01)

(56) References Cited

U.S. PATENT DOCUMENTS

| | | | |
|---|---|---|---|
| 6,993,384 | B2 | 1/2006 | Bradley et al. |
| 7,539,538 | B2 | 5/2009 | Parramon et al. |
| 7,650,184 | B2 | 1/2010 | Walter |
| 7,974,706 | B2 | 7/2011 | Moffitt et al. |
| 7,987,000 | B2 | 7/2011 | Moffitt et al. |
| 8,019,439 | B2 | 9/2011 | Kuzma et al. |
| 2003/0139781 | A1 | 7/2003 | Bradley et al. |
| 2005/0267546 | A1 | 12/2005 | Parramon et al. |
| 2007/0150036 | A1 | 6/2007 | Anderson |
| 2007/0168004 | A1 | 7/2007 | Walter |
| 2007/0168007 | A1 | 7/2007 | Kuzma et al. |
| 2007/0208394 | A1 | 9/2007 | King et al. |
| 2010/0057162 | A1 | 3/2010 | Moffitt et al. |
| 2010/0100153 | A1 | 4/2010 | Carlson et al. |
| 2011/0009927 | A1 | 1/2011 | Parker et al. |
| 2011/0264165 | A1 | 10/2011 | Molnar et al. |
| 2012/0035493 | A1 | 2/2012 | Gutfinger et al. |
| 2013/0304152 | A1 | 11/2013 | Bradley et al. |
| 2014/0005752 | A1 | 1/2014 | Hershey |

OTHER PUBLICATIONS

"U.S. Appl. No. 13/930,493, Final Office Action mailed Jan. 21, 2016", 7 pgs.

"U.S. Appl. No. 13/930,493, Final Office Action mailed Mar. 16, 2015", 7 pgs.

"U.S. Appl. No. 13/930,493, Non Final Office Action mailed Aug. 14, 2015", 7 pgs.

"U.S. Appl. No. 13/930,493, Non Final Office Action mailed Oct. 2, 2014", 7 pgs.

"U.S. Appl. No. 13/930,493, Notice of Allowance mailed Mar. 31, 2016", 7 pgs.

"U.S. Appl. No. 13/930,493, Preliminary Amendment filed Jun. 28, 2013", 8 pgs.

"U.S. Appl. No. 13/930,493, Respone filed Dec. 14, 2015 to Non Final Office Action mailed Aug. 14, 2015", 9 pgs.

"U.S. Appl. No. 13/930,493, Response filed Mar. 18, 2016 to Final Office Action mailed Jan. 21, 2016", 8 pgs.

"U.S. Appl. No. 13/930,493, Response filed May 18, 2015 to Final Office Action mailed Mar. 16, 2015", 9 pgs.

"International Application Serial No. PCT/US2013/048577, International Preliminary Report on Patentability mailed Jan. 8, 2015", 9 pgs.

"International Application Serial No. PCT/US2013/048577, International Search Report mailed Oct. 15, 2013", 6 pgs.

"International Application Serial No. PCT/US2013/048577, Written Opinion mailed Oct. 15, 2013", 7 pgs.

HIGH FREQUENCY NEUROMODULATION SYSTEM AND METHOD FOR REDUCING ENERGY REQUIREMENTS

RELATED APPLICATION DATA

The present application is a continuation of U.S. application Ser. No. 13/930,493, filed Jun. 28, 2013, which claims the benefit under 35 U.S.C. §119 to U.S. provisional patent application Ser. No. 61/666,568, filed Jun. 29, 2012. The foregoing application is hereby incorporated by reference into the present application in its entirety.

FIELD OF THE INVENTION

The present inventions relate to tissue modulation systems, and more particularly, to systems and methods for adjusting the modulation provided to tissue to minimize the energy requirements of the systems.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of spinal modulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neuromodulation systems typically includes one or more electrode carrying modulation leads, which are implanted at the desired stimulation site, and a neuromodulation device implanted remotely from the stimulation site, but coupled either directly to the modulation lead(s) or indirectly to the modulation lead(s) via a lead extension. Thus, electrical pulses can be delivered from the neuromodulation device to the electrode(s) to activate a volume of tissue in accordance with a set of modulation parameters and provide the desired efficacious therapy to the patient. In particular, electrical energy conveyed between at least one cathodic electrode and at least one anodic electrode creates an electrical field, which when strong enough, depolarizes (or "stimulates") the neurons beyond a threshold level, thereby inducing the firing of action potentials (APs) that propagate along the neural fibers. A typical modulation parameter set may include the electrodes that are sourcing (anodes) or returning (cathodes) the modulating current at any given time, as well as the amplitude, duration, and rate of the stimulation pulses.

The neuromodulation system may further comprise a handheld patient programmer to remotely instruct the neuromodulation device to generate electrical stimulation pulses in accordance with selected modulation parameters. The handheld programmer in the form of a remote control (RC) may, itself, be programmed by a clinician, for example, by using a clinician's programmer (CP), which typically includes a general purpose computer, such as a laptop, with a programming software package installed thereon.

Of course, neuromodulation devices are active devices requiring energy for operation, and thus, the neuromodulation system may oftentimes includes an external charger to recharge a neuromodulation device, so that a surgical procedure to replace a power depleted neuromodulation device can be avoided. To wirelessly convey energy between the external charger and the implanted neuromodulation device, the charger typically includes an alternating current (AC) charging coil that supplies energy to a similar charging coil located in or on the neuromodulation device. The energy received by the charging coil located on the neuromodulation device can then be used to directly power the electronic componentry contained within the neuromodulation device, or can be stored in a rechargeable battery within the neuromodulation device, which can then be used to power the electronic componentry on-demand.

Typically, the therapeutic effect for any given neuromodulation application may be optimized by adjusting the modulation parameters. Often, these therapeutic effects are correlated to the diameter of the nerve fibers that innervate the volume of tissue to be modulated. For example, in SCS, activation (i.e., recruitment) of large diameter sensory fibers is believed to reduce/block transmission of smaller diameter pain fibers via interneuronal interaction in the dorsal horn of the spinal cord. Activation of large sensory fibers also typically creates a sensation known as paresthesia that can be characterized as an alternative sensation that replaces the pain signals sensed by the patient.

Although alternative or artifactual sensations are usually tolerated relative to the sensation of pain, patients sometimes report these sensations to be uncomfortable, and therefore, they can be considered an adverse side-effect to neuromodulation therapy in some cases. It has been shown that high-frequency pulsed electrical energy can be effective in providing neuromodulation therapy for chronic pain without causing paresthesia. In contrast to conventional neuromodulation therapies, which employ low- to mid-frequencies (e.g., 2-250 Hz) to provide a one-to-one correspondence between the generation of an AP and each electrical pulse, high frequency modulation (e.g., 1 KHz-50 KHz) can be employed to block naturally occurring APs within neural fibers or otherwise disrupt the APs within the neural fibers. Although high-frequency modulation therapies have shown good efficacy in early studies, one notable drawback is the relatively high energy requirement to achieve high-frequency modulation in contrast to low- to mid-frequency modulation. In particular, the amount of energy required to generate an electrical waveform is proportional to the frequency of the electrical waveform. Thus, neuromodulation devices that generate relatively low frequency modulation energy typically need to be recharged only once every 1-2 weeks, whereas neuromodulation devices that generate relatively high frequency modulation energy may require a daily or more frequent recharge.

There, thus, remains a need to decrease the energy requirements for high-frequency neuromodulation therapy.

SUMMARY OF THE INVENTION

In accordance with a first aspect of the present inventions, an electrical neuromodulation system is provided. The neuromodulation system comprises a neuromodulation device capable of delivering electrical energy between electrodes at a defined frequency. The neuromodulation system further comprises control/processing circuitry configured for instructing the neuromodulation device to deliver the electrical energy at a first frequency to a first set of electrodes having a first combined electrode impedance, and automatically selecting a second set of electrodes having a second combined electrode impedance. Significantly, the combined electrode impedance of the second set of electrodes is less than the combined electrode impedance of the first set of electrodes to provide a more efficient means of delivering the electrical modulation energy during at the higher frequency.

In one embodiment, the control/processing circuitry is configured for automatically selecting the second set of electrodes by adding at least one electrode to the first set of electrodes without subtracting any electrode from the first set of electrodes. In another embodiment, the control/processing is configured for automatically selecting the second set of electrodes by replacing an electrode of the first set of electrodes with another electrode having an individual electrode impedance that is lower than an individual electrode impedance of the replaced electrode. The neuromodulation system may optionally comprise a user interface configured for allowing a user to enter a value corresponding to the second frequency, in which case, the control/processing circuitry may be configured for automatically selecting the set of electrodes in response to the user entry of the value.

The control/processing circuitry is further configured for instructing the neuromodulation device to deliver the electrical energy at a second frequency to the second set of electrodes. The second frequency is equal to or greater than the first frequency. For example, the first frequency may be less than 1 KHz (e.g., in the range of 2 Hz-250 Hz), and the second frequency may be greater than or equal to 1 KHz (e.g., in the range of 1 KHz-50 KHz).

The control/processing circuitry may be contained in the neuromodulation device or an external control device. In an optional embodiment, the system further comprises a battery configured for storing power used to generate the electrical energy. The neuromodulation system may include additional features that increase the efficiency of the high frequency neuromodulation. For example, the neuromodulation system may further comprise a more efficient cuff lead or a surgical paddle lead that carries the electrodes. Or the neuromodulation system may further comprise a coating disposed on the electrodes that increases the capacitances of the electrodes.

In accordance with a second aspect of the present inventions, a method of treating an ailment (e.g., chronic pain) of a patient using a neuromodulation device is provided. The method comprises delivering electrical modulation energy at a first frequency from the neuromodulation device to a first set of electrodes having a first combined electrode impedance, and automatically selecting a second set of electrodes having a second combined electrode impedance. Significantly, the combined electrode impedance of the second set of electrodes is less than the combined electrode impedance of the first set of electrodes to provide a more efficient means of delivering the electrical modulation energy during at the higher frequency.

In one embodiment, the control/processing circuitry is configured for automatically selecting the second set of electrodes by adding at least one electrode to the first set of electrodes without subtracting any electrode from the first set of electrodes. In another embodiment, the control/processing is configured for automatically selecting the second set of electrodes by replacing an electrode of the first set of electrodes with another electrode having an individual electrode impedance that is lower than an individual electrode impedance of the replaced electrode. The method further comprises delivering the electrical modulation energy at a second frequency to the second set of electrodes. The second frequency is equal to or greater than the first frequency. For example, the first frequency may be less than 1 KHz (e.g., in the range of 2 Hz-250 Hz), and the second frequency may be greater than or equal to 1 KHz (e.g., in the range of 1 KHz-50 KHz).

One method automatically selects the second set of electrodes by adding at least one electrode to the first set of electrodes without subtracting any electrode from the first set of electrodes. Another method automatically selects the second set of electrodes by replacing an electrode of the first set of electrodes with another electrode having an individual electrode impedance that is lower than an individual electrode impedance of the replaced electrode. An optional method comprises receiving a value corresponding to the second frequency from a user, and automatically selecting the second set of electrodes in response to the user entry of the value.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal column modulation (SCM) system. However, it is to be understood that the while the invention lends itself well to applications in SCM, the invention, in its broadest aspects, may not be so limited. Rather, the invention may be used with any type of implantable electrical circuitry used to modulate tissue. For example, the present invention may be used as part of a pacemaker, a defibrillator, a cochlear modulator device, a retinal modulator device, a modulator device configured to produce coordinated limb movement, a cortical modulator device, a deep brain modulator device, peripheral nerve modulator device, micromodulator device, or in any other tissue modulator device configured to treat urinary incontinence, sleep apnea, shoulder sublaxation, headache, etc.

Figure 1:
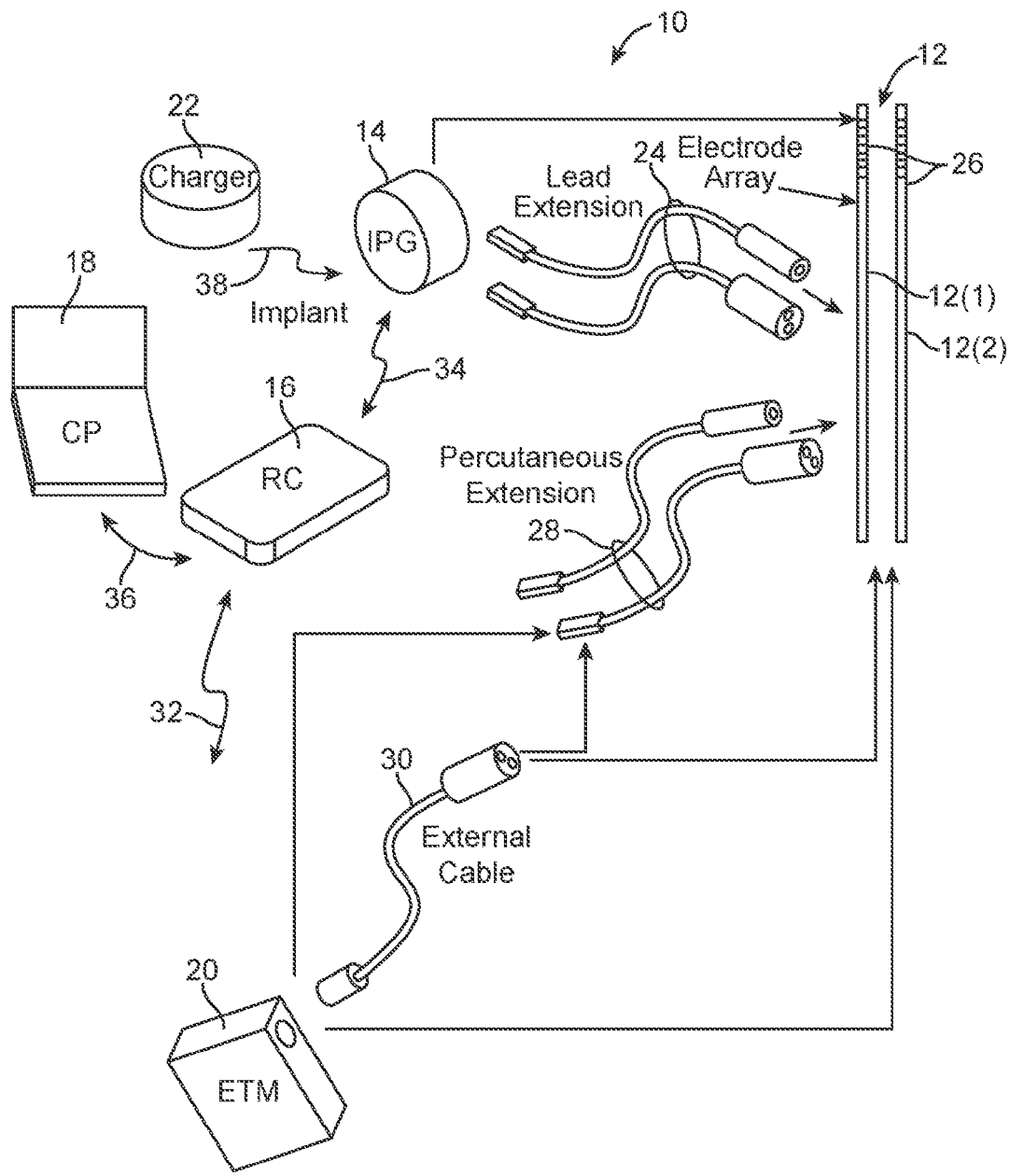
FIG. 1 is plan view of one embodiment of a spinal column modulation (SCM) system arranged in accordance with the present inventions.

Turning first to FIG. 1, an exemplary SCM system 10 generally includes one or more (in this case, two) implantable modulation leads 12(1) and 12(2), an implantable pulse generator (IPG) 14, an external remote controller RC 16, a clinician's programmer (CP) 18, an External Trial Modulator (ETM) 20, and an external charger 22.

The IPG 14 is physically connected via one or more percutaneous lead extensions 24 to the modulation leads 12, which carry a plurality of electrodes 26 arranged in an array. In the illustrated embodiment, the modulation leads 12 are percutaneous leads, and to this end, the electrodes 26 are arranged in-line along the modulation leads 12. As will be described in further detail below, in alternative embodiments, the electrodes 26 may be arranged in a two-dimensional pattern on a single paddle lead or arranged in a circular pattern on a cuff lead. As will be described in further detail below, the IPG 14 includes pulse generation circuitry that delivers the electrical modulation energy in the form of an electrical pulse train to the electrode array 26 in accordance with a set of modulation parameters.

The ETM 20 may also be physically connected via the percutaneous lead extensions 28 and external cable 30 to the modulation leads 12. The ETM 20, which has similar pulse generation circuitry as the IPG 14, also delivers electrical modulation energy in the form of an electrical pulse train to the electrode array 26. The major difference between the ETM 20 and the IPG 14 is that the ETM 20 is a non-implantable device that is used on a trial basis after the modulation leads 12 have been implanted and prior to implantation of the IPG 14, to test the responsiveness of the modulation that is to be provided. Thus, any functions described herein with respect to the IPG 14 can likewise be performed with respect to the ETM 20. Further details of an exemplary ETM are described in U.S. Pat. No. 6,895,280, which is expressly incorporated herein by reference.

The RC 16 may be used to telemetrically control the ETM 20 via a bi-directional RF communications link 32. Once the IPG 14 and modulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. The CP 18 provides clinician detailed modulation parameters for programming the IPG 14 and ETM 20 in the operating room and in follow-up sessions. The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
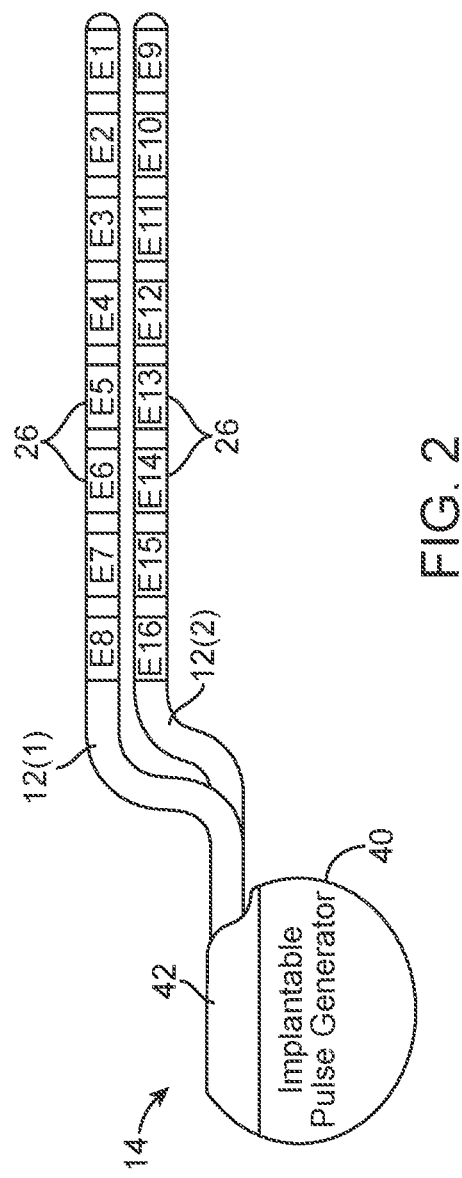
FIG. 2 is a profile view of an implantable pulse generator (IPG) and percutaneous leads used in the SCS system of FIG. 1.

Referring to FIG. 2, the IPG 14 comprises an outer case 40 for housing the electronic and other components (described in further detail below), and a connector 42 to which the proximal end of the neuromodulation leads 12 mate in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

In the embodiment illustrated in FIG. 2, the neurostimulation leads 12 take the form of percutaneous leads on which the electrodes 26 (in this case, electrodes E1-E16) are disposed as ring electrodes. In the illustrated embodiment, two percutaneous leads 12(1) and 12(2) on which electrodes E1-E8 and E9-E16 are respectively disposed can be used with the SCM system 10. The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Figure 3:
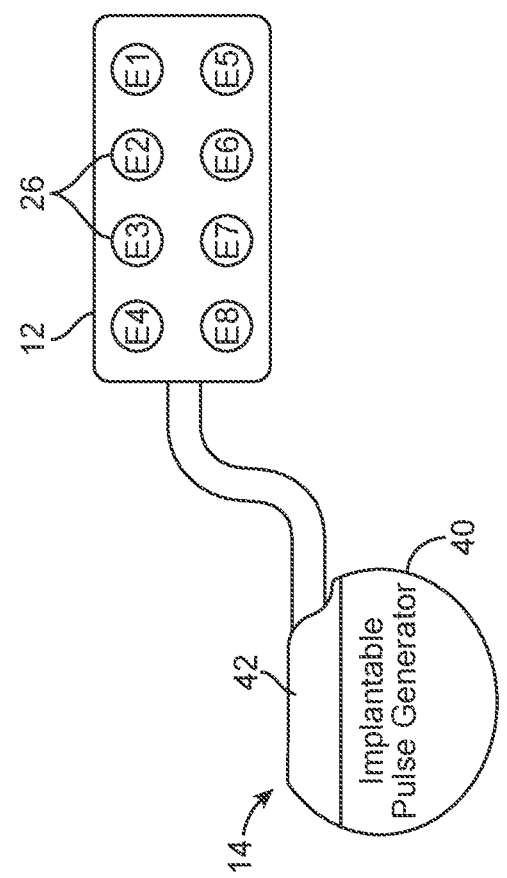
FIG. 3 is a profile view of an implantable pulse generator (IPG) and a surgical paddle lead used in the SCS system of FIG. 1.

In an alternative embodiment illustrated in FIG. 3, the neurostimulation lead 12 takes the form of a surgical paddle lead 12 on which the electrodes 26 (in this case, electrodes E1-E8) are carried. The electrodes 26 are arranged in a two-dimensional array in two columns along the axis of the neurostimulation lead 12. In the illustrated embodiment, the electrodes 26 are arranged in two columns of electrodes 26 (electrodes E1-E4 in the first column, and electrodes E5-E8 in the second column). The actual number of leads and electrodes will, of course, vary according to the intended application. The surgical paddle design facilitates placement of the modulating electrodes in regions intra-spinally, intracranially, or subcutaneously where separation between the electrodes and the nerves of interest is minimized (e.g., minimal cerebral spinal fluid thickness, epidural, and close to nerve roots (i.e., "in the gutter"). Preferably, the electrodes have a large surface area to reduce the impedance and thus, the necessarily energy consumption. Further details regarding the construction and method of manufacture of surgical paddle leads are disclosed in U.S. patent application Ser. No. 11/319,291, entitled "Stimulator Leads and Methods for Lead Fabrication," and U.S. patent application Ser. No. 12/204,094, entitled "Multiple Tunable Central Cathodes on a Paddle for Increased Medial-Lateral and Rostro-Caudal Flexibility via Current Steering, the disclosures of which are expressly incorporated herein by reference.

Figure 4:
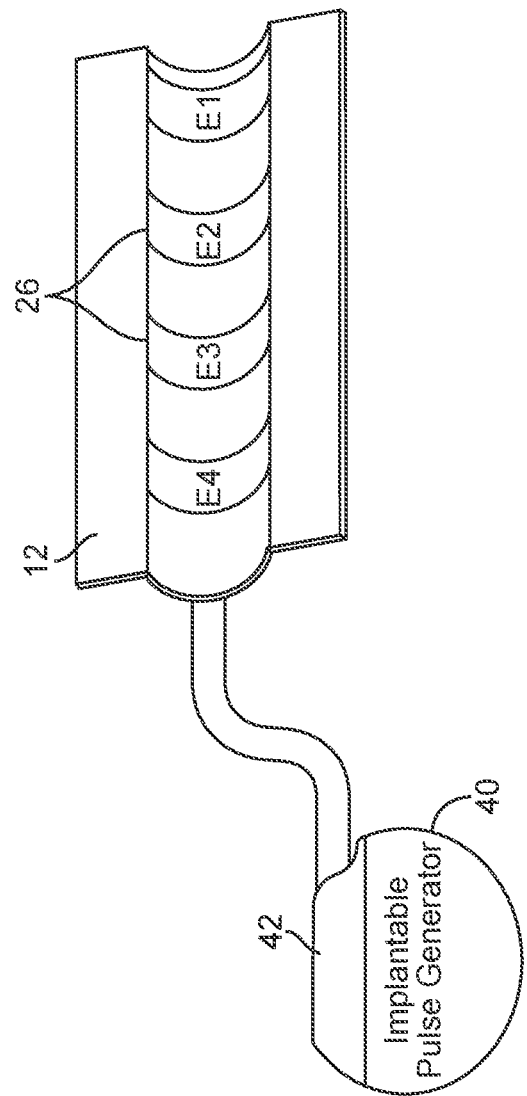
FIG. 4 is a profile view of an implantable pulse generator (IPG) and a cuff lead used in the SCS system of FIG. 1.

In another alternative embodiment illustrated in FIG. 4, the neurostimulation lead 12 takes the form of a cuff lead 12 on which the electrodes 26 (in this case, electrodes E1-E4) are carried. The electrodes 26 are arranged in a linear array around the arc of the cuff. The actual number of leads and electrodes will, of course, vary according to the intended application. The cuff design minimizes the separation between the modulating electrodes and the target tissue. This cuff design can be used to modulate any nerve bundle or fiber tract on or around which the cuff can be implanted. Further details regarding the construction and method of manufacture of cuff leads are disclosed in U.S. Pat. No. 7,974,706, entitled "Electrode Contact Configurations for Cuff Leads," the disclosure of which is expressly incorporated herein by reference.

The electrodes 26 of the percutaneous leads, surgical paddle lead, or cuff lead may be composed or modified in a manner that decreases their impedance during high frequency neuromodulation. Increased impedances decrease efficiency of delivery electrical energy to the target tissue. For example, the non-metallic (e.g., conductive polymer) electrodes and/or conductor compositions may improve efficiencies in high frequency modulation applications by removing some of the constraints due to the material properties of metals, such as stiffness, which may not provide adequate conformance to the neural tissue, thereby possibly increasing neuromodulatory thresholds. Optionally, treatments, and coatings can be applied to the electrodes 26 to reduce impedance due in part to high frequency neuromodulation. The coatings may include steroid elutants to minimize fibrotic growth, which can lead to increased impedances. Iridium Oxide, Titanium Nitride, or other similar coatings that increase total surface area may be used as coatings, which change the dielectric between tissue and the electrodes 26, thereby increasing the capacitance of the electrodes 26, thus, minimizing the modulation energy and energy consumption.

As will be described in further detail below, the IPG 14 includes pulse generation circuitry that provides electrical modulation energy to the electrodes 26 in accordance with a set of modulation parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes), pulse width (measured in microseconds), pulse rate (measured in pulses per second), duty cycle (pulse width divided by cycle duration), burst rate (measured as the modulation energy on duration X and modulation energy off duration Y), and pulse shape.

With respect to the pulse patterns provided during operation of the SCM system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 40, so that the electrical current has a path from the energy source contained within the IPG case 40 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 40 of the IPG 14, so that electrical energy is transmitted between the selected electrode 26 and case 40. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

The electrical energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) modulation pulse and an anodic (positive) recharge pulse that is generated after the modulation pulse to prevent direct current charge transfer through the tissue, thereby avoiding electrode degradation and cell trauma.

That is, charge is conveyed through the electrode-tissue interface via current at an electrode during a modulation period (the length of the modulation pulse), and then pulled back off the electrode-tissue interface via an oppositely polarized current at the same electrode during a recharge period (the length of the recharge pulse). The recharge pulse may be active, in which case, the electrical current is actively conveyed through the electrode via current or voltage sources, or the recharge pulse may be passive, in which case, the electrical current may be passively conveyed through the electrode via redistribution of the charge flowing from coupling capacitances present in the circuit.

Figure 5:
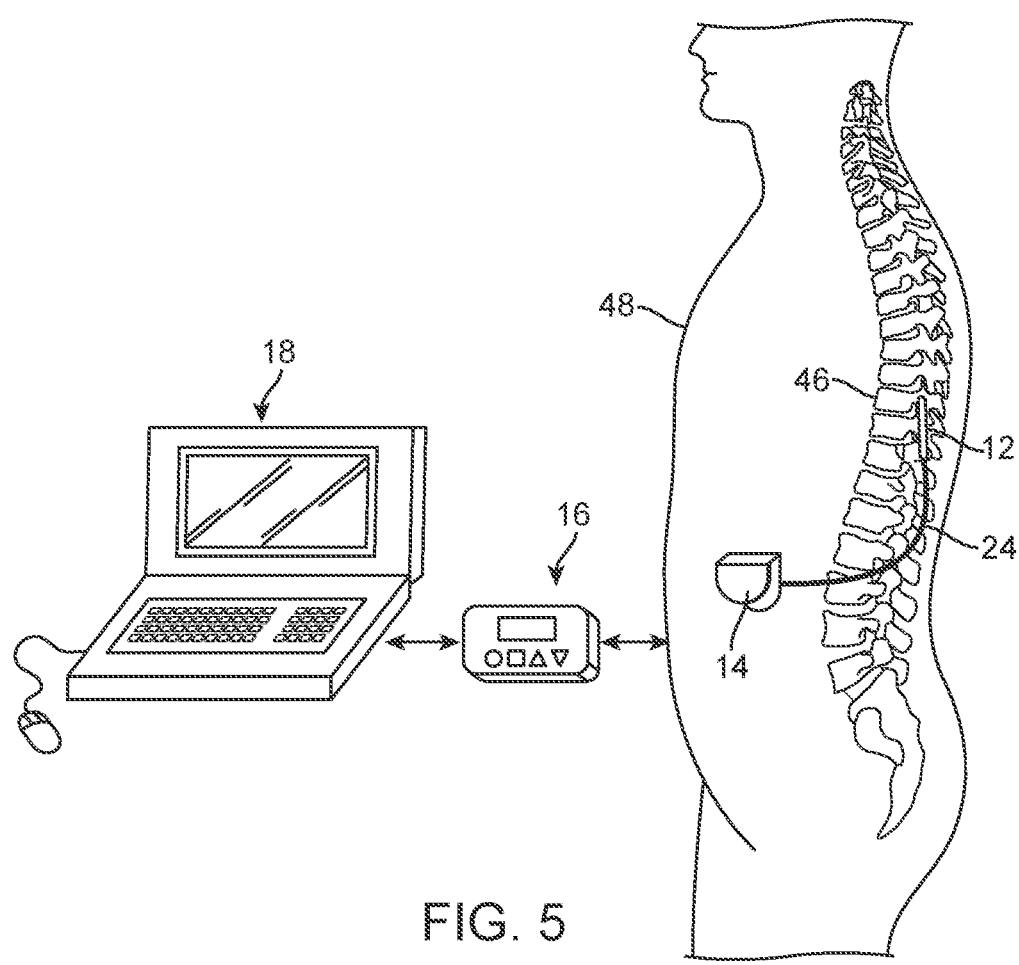
FIG. 5 is a plan view of the SCM system of FIG. 1 in use with a patient.

As shown in FIG. 5, the modulation leads (or lead) 12 are implanted within the spinal column 46 of a patient 48. The preferred placement of the modulation leads 12 is adjacent, i.e., resting near, or upon the dura, adjacent to the spinal cord area to be stimulated. The modulation leads 12 will be located in a vertebral position that depends upon the location and distribution of the chronic pain. For example, if the chronic pain is in the lower back or legs, the modulation leads 12 may be located in the mid- to low-thoracic region (e.g., at the T9-12 vertebral levels). Due to the lack of space near the location where the electrode leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Significantly, the SCM system 10 utilizes a technique that dynamically decreases the electrode impedance of the electrodes 26 when the frequency, and in this case, the pulse rate, of the electrical neuromodulation energy is increased from a relatively low value to a relatively high value. An electrode impedance is the overall resistance to the flow of electrons caused by the IPG 14, leads 12, electrode-tissue interface, and intervening tissue between the anode(s) and cathode(s). Electrode impedance can be measured by sourcing current (I) from an electrode and measuring the voltage (V) on that same electrode, and then computing the impedance (also known as resistance, or R) in accordance with the equation R=V/I (Ohm's Law). Electrode impedance can be an individual impedance, meaning that only one impedance at a single electrode is considered, or a combined impedance, in which case the combined parallel impedance of one or more electrodes is considered.

In the preferred embodiment, the SCM system 10 seeks to reduce the combined electrode impedance of the electrodes during relatively high frequency neuromodulation. By reducing the combined electrode impedance, electrical modulation energy may be delivered more efficiency during high frequency neuromodulation, thereby positively impacting battery life and/or recharge interval. In this manner, the electrical modulation energy may be delivered using a modulation parameter that positively impacts battery life and/or recharge interval.

To this end, the SCM system 10 instructs the IPG 14 to deliver electrical energy at a first lower frequency (e.g., less than 1 KHz, and preferably in the range of 2 Hz-250 Hz) to a first set of electrodes, automatically selects a second set of electrodes, and instructs the IPG 14 to deliver electrical energy at a second higher frequency (e.g., greater than 1 KHz, and preferably in the range of 1 KHz-50 KHz) to the second electrode set. The second set of electrodes has a combined electrode impedance that is lower than first set of electrodes, thereby providing for a more efficient delivery of the higher frequency neuromodulation energy. In the preferred embodiment, the SCM system 10 automatically selects the second electrode set in response to a user entry of an increase in the frequency of the neuromodulation energy delivery. Alternatively, the SCM system 10 may automatically select the second electrode set and automatically increase the frequency of the neuromodulation energy delivery without user intervention.

Figure 6C:
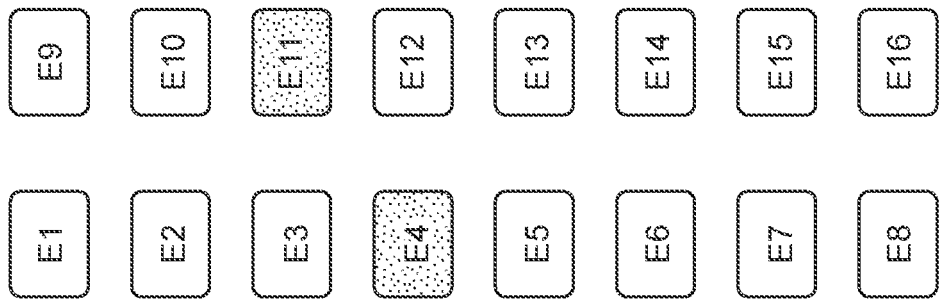
FIG. 6*c* is a plan view of another electrode set to which electrical modulation energy can be conveyed at a relatively high frequency.

In one embodiment, the SCM system 10 may select the second electrode set by adding at least one electrode to the first set of electrodes without subtracting any electrode from the first set of electrodes. For example, with reference to FIG. 6a, a first set of electrodes to which electrical neuromodulation energy is delivered includes electrodes E4 and E12. Although, in the illustrated embodiment, electrodes E4 and E12 are cathodic, and therefore, cathodic electrical energy is delivered to the electrodes E4 and E12, electrodes E4 and E12 may be anodic, in which case, anodic electrical energy is delivered to the electrodes E4 and E12. Electrodes E4 and E12 may form part of a monopolar arrangement wherein the case electrode 40 (shown in FIGS. 2-4) forms the anodic portion of the monopolar arrangement, or may form part of a bipolar arrangement wherein others of the lead electrodes E4 and E12 form the anodic portion of the bipolar arrangement.

Figure 6B:
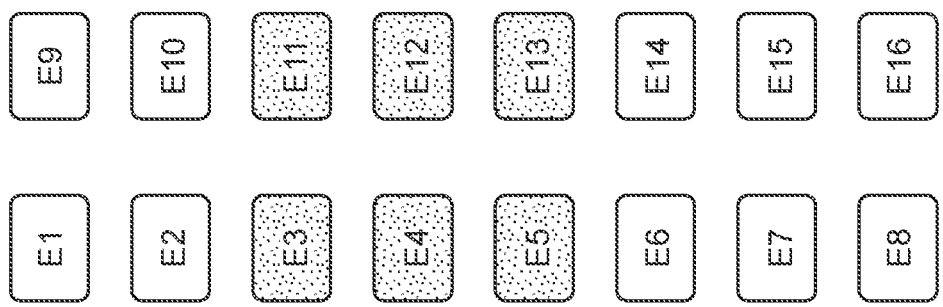
FIG. 6*b* is a plan view of an electrode set to which electrical modulation energy can be conveyed at a relatively high frequency.
Figure 6A:
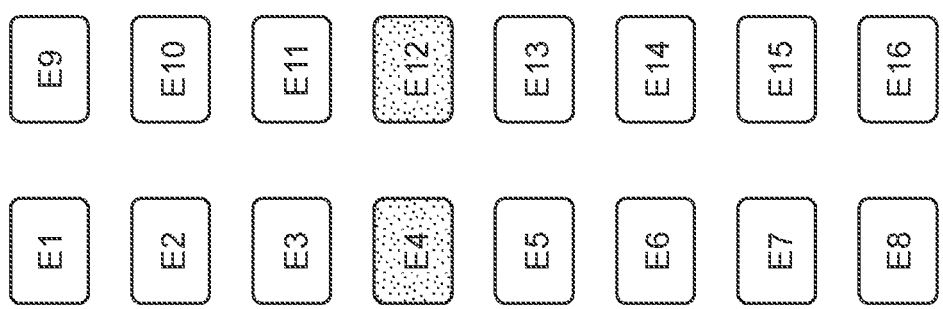
FIG. 6*a* is a plan view of an electrode set to which electrical modulation energy can be conveyed at a relatively low frequency.

With reference to FIG. 6b, a second set of electrodes (E3-E5 and E11-E13) can be created by adding electrodes E3, E11, E5, and E13 to the first electrode set. By increasing the number of electrodes, it can be appreciated that the combined electrode impedance of the second electrode set is less than the combined electrode impedance of the first electrode set. As such, the electrical modulation energy can be more efficiently delivered from the IPG 14 to the second electrode set at the relatively high frequency, thereby minimizing energy consumption within the IPG 14. Notably, although the smaller first set of electrodes (E4 and E12) may focus the electrical modulation energy at a particular target site adjacent these electrodes, thereby providing an efficient means for providing the necessary therapy at relative low neuromodulation frequencies, high frequency neuromodulation does not require the electrical modulation energy to be focused at a particular target site in order to efficaciously provided therapy to the patient. As such, the use of the larger second electrode set for high frequency neuromodulation will not significantly diminish the efficacy of the resulting therapy. Additional sets of electrodes with increasing numbers of electrodes may be created as the frequency of the neuromodulation increases.

In another embodiment, the SCM system 10 may select the second electrode set by replacing an electrode of the first electrode set with another electrode having an individual electrode impedance that is lower than an individual electrode impedance the replaced electrodes. For example, with reference to FIG. 6c, a second set of electrodes (E4 and E11) can be created by replacing electrode E12, which has a relatively large electrode impedance (500 ohms) with electrode E11, which has a relatively small electrode impedance (250 ohms). As a result, the combined electrode impedance of the second set of electrodes is less than the combined electrode impedance of the first electrode set. Again, by accomplishing this, the electrical modulation energy can be more efficiently delivered from the IPG 14 to the second electrode set at the relatively high frequency, thereby minimizing energy consumption within the IPG 14. Notably, although electrode E12 may be better located at the particular target site, thereby providing an efficient means for providing the necessary therapy at relative low neuromodulation frequencies, again, high frequency neuromodulation does not require the electrical modulation energy to be focused at a particular target site in order to efficaciously provided therapy to the patient. As such, the replacement of the electrode E12, which is closer to the target site, with electrode E11, which is further from the target site, will not significantly diminish the efficacy of the resulting therapy.

As will be described in further detail below, the controller/processor that performs the function of reducing the combined electrode impedance of the active electrodes can be contained either in the IPG 14 or the RC 16, or even the CP 18.

Figure 7:
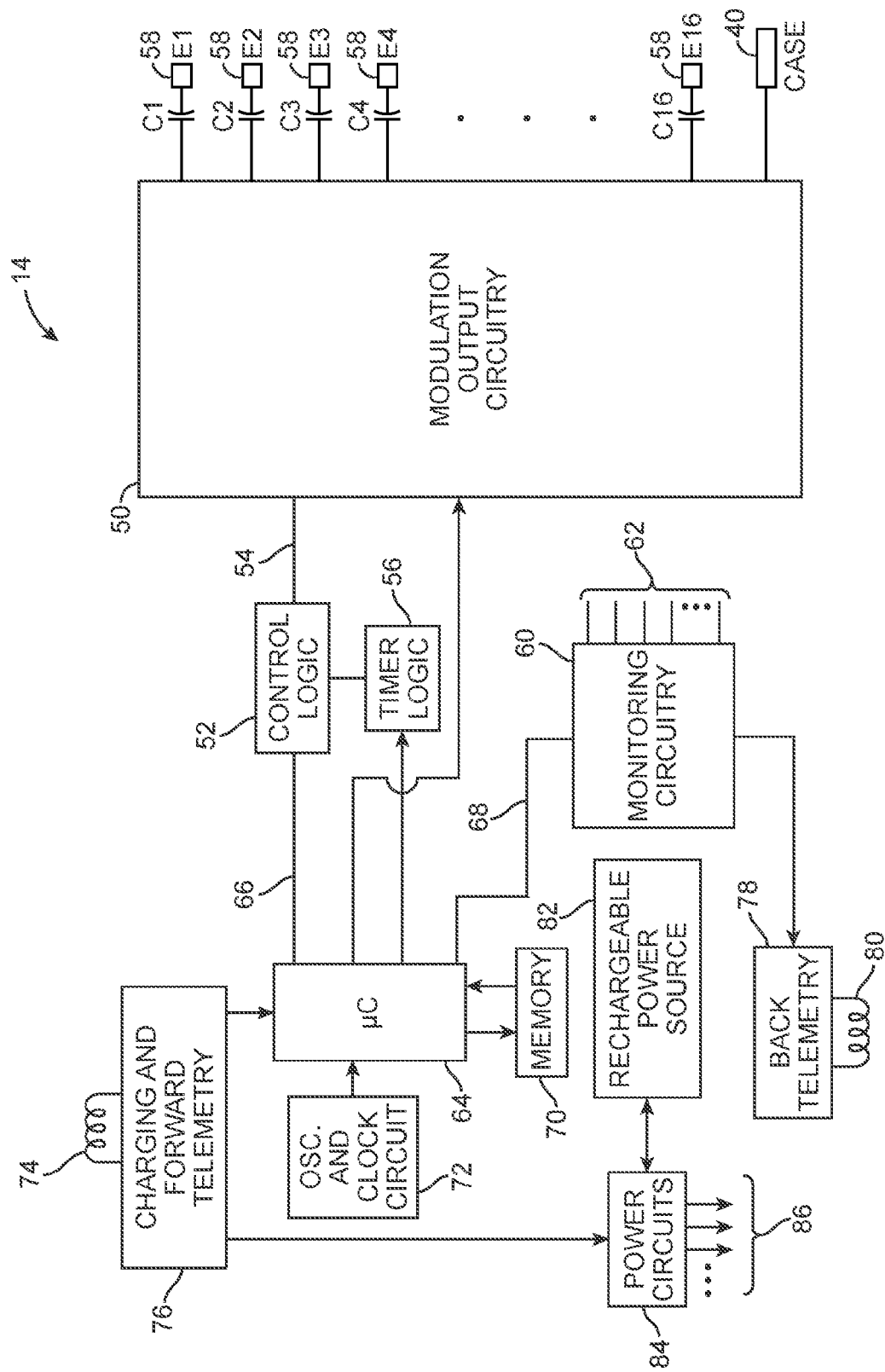
FIG. 7 is a block diagram of the internal components of the IPG of FIGS. 2-4.

Turning next to FIG. 7, the internal components of the IPG 14 will now be described. The IPG 14 includes modulation output circuitry 50 configured for generating electrical modulation energy in accordance with an electrical pulse train having a specified pulse amplitude, pulse rate, pulse width, duty cycle, burst rate, and shape under control of control logic 52 over data bus 54. Control of the pulse rate and duration is facilitated by analog circuitry, or digital timer logic circuitry 56 controlling the analog circuitry, and which may have a suitable resolution, e.g., 10 μs. In alternative embodiments, a continuous modulating waveform may be generated by the modulation output circuitry 50 in a manner described in U.S. Provisional Patent Application Ser. No. 61/646,773, entitled "System and Method for Shaped Phased Current Delivery," which is expressly incorporated herein by reference. The modulation energy generated by the modulation output circuitry 50 is output via capacitors C1-C16 to electrical terminals 58 corresponding to electrodes E1-E16.

The modulation output circuitry 50 may either comprise independently controlled current sources for providing stimulation pulses of a specified and known amperage to or from the electrical terminals 58, or independently controlled voltage sources for providing stimulation pulses of a specified and known voltage at the electrical terminals 58 or to multiplexed current or voltage sources that are then connected to the electrical terminals 58. The operation of this modulation output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 also comprises monitoring circuitry 60 for monitoring the status of various nodes or other points 62 throughout the IPG 14, e.g., power supply voltages, temperature, battery voltage, and the like. The IPG 14 further comprises processing circuitry in the form of a microcontroller (µC) 64 that controls the control logic 52 over data bus 66, and obtains status data from the monitoring circuitry 60 via data bus 68. The IPG 14 additionally controls the timer logic 56. The IPG 14 further comprises memory 70 and oscillator and clock circuit 72 coupled to the microcontroller 64. The microcontroller 64, in combination with the memory 70 and oscillator and clock circuit 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and modulation parameters. In controlling the operation of the IPG 14, the microcontroller 64 is able to individually generate electrical energy at the electrodes 26 using the modulation output circuitry 50, in combination with the control logic 52 and timer logic 56, thereby allowing each electrode 26 to be paired or grouped with other electrodes 26, including the monopolar case electrode, to control the polarity, pulse amplitude, pulse rate, pulse width, and pulse duty cycle through which the electrical energy is provided.

The IPG 14 further comprises an alternating current (AC) receiving coil 74 for receiving programming data (e.g., the operating program and/or modulation parameters) from the RC 16 and/or CP 18 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14. Notably, to the extent that the microcontroller 64 is used to perform the control/processing functions of the energy consumption minimization techniques described above, the user entry of the pulse rate (or frequency) adjustment into the RC 16 or the CP 18 can be received from the RC 16 or CP 18 via the coil 74 and forward telemetry circuitry 76, and the energy efficient electrode set or sets selected by the microcontroller 64 in response to the user entered pulse rate adjustment can be stored in the memory 70. For example, the electrode set(s) may be stored in the memory 70 during a fitting session performed at the clinician's office. Alternatively, the microcontroller 64 may dynamically create the electrode set(s) as the user entry of the pulse rate is received without storing the electrode set(s) within the memory 70.

The IPG 14 further comprises back telemetry circuitry 78 and an alternating current (AC) transmission coil 80 for sending informational data sensed through the monitoring circuitry 60 to the RC 16 and/or CP 18. The back telemetry features of the IPG 14 also allow its status to be checked. For example, when the RC 16 and/or CP 18 initiates a programming session with the IPG 14, the capacity of the battery is telemetered, so that the RC 16 and/or CP 18 can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18.

The IPG 14 further comprises a rechargeable power source 82 and power circuits 84 for providing the operating power to the IPG 14. The rechargeable power source 82 may, e.g., comprise a lithium-ion or lithium-ion polymer battery. The rechargeable battery 82 provides an unregulated voltage to the power circuits 84. The power circuits 84, in turn, generate the various voltages 86, some of which are regulated and some of which are not, as needed by the various circuits located within the IPG 14. The rechargeable power source 82 is recharged using rectified AC power (or DC power converted from AC power through other means, e.g., efficient AC-to-DC converter circuits, also known as "inverter circuits") received by the AC receiving coil 74. To recharge the power source 82, an external charger (not shown), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCM system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the modulation in accordance with the control signals.

Figure 8:
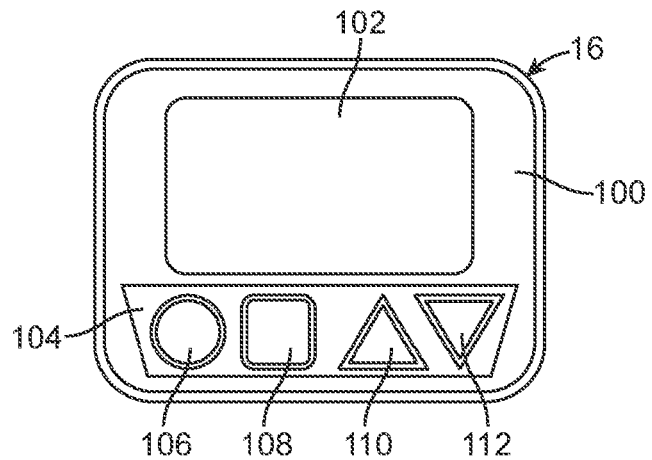
FIG. 8 is a plan view of a hand-held remote control (RC) that can be used in the SCM system of FIG. 1.

Referring now to FIG. 8, one exemplary embodiment of an RC 16 will now be described. As previously discussed, the RC 16 is capable of communicating with the IPG 14, CP 18, or ETM 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of modulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 106 to switch between screen displays and/or parameters. The buttons 110 and 112 serve as up/down buttons that can be actuated to increase or decrease any of modulation parameters of the pulse generated by the IPG 14, including the pulse amplitude, pulse width, and pulse rate. For example, the selection button 108 can be actuated to place the RC 16 in a "Pulse Amplitude Adjustment Mode," during which the pulse amplitude can be adjusted via the up/down buttons 110, 112, a "Pulse Width Adjustment Mode," during which the pulse width can be adjusted via the up/down buttons 110, 112, and a "Pulse Rate Adjustment Mode," during which the pulse rate can be adjusted via the up/down buttons 110, 112. Alternatively, dedicated up/down buttons can be provided for each stimulation parameter. Rather than using up/down buttons, any other type of actuator, such as a dial, slider bar, or keypad, can be used to increment or decrement the stimulation parameters. Significant to the present inventions, the selection button 108 can also be actuated to place the SCM system 10 in an "Energy Minimization" mode that minimizes the energy consumption of the IPG 14 when delivering the therapeutic electrical energy at relatively high frequencies. When the SCM system 10 is not in the "Energy Minimization" mode, the SCM system 10 operates in a conventional manner by maintaining the same electrode combination when the pulse rate is adjusted between relatively low frequencies and relatively high frequencies.

Figure 9:
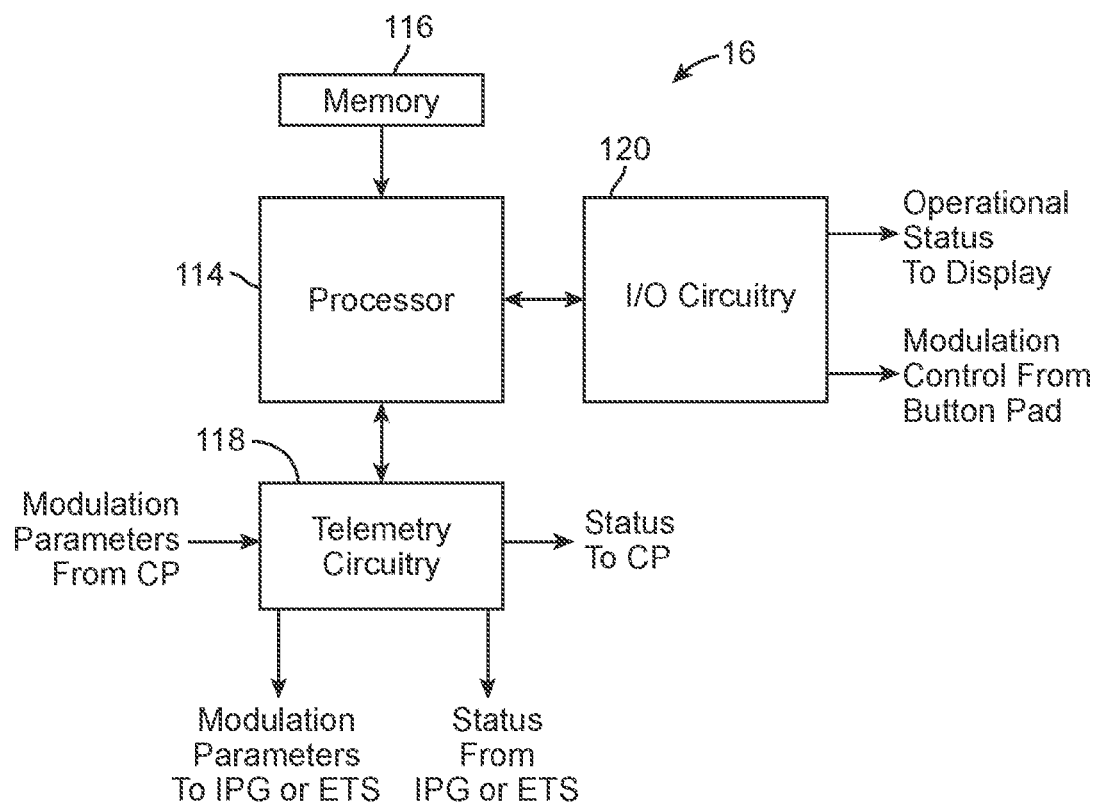
FIG. 9 is a block diagram of the internal components of the RC of FIG. 5.

Referring to FIG. 9, the internal components of an exemplary RC 16 will now be described. The RC 16 generally includes a processor 114 (e.g., a microcontroller), memory 116 that stores an operating program for execution by the processor 114, as well as modulation parameters, input/output circuitry, and in particular, telemetry circuitry 118 for outputting modulation parameters to the IPG14 and receiving status information from the IPG 14, and input/output circuitry 120 for receiving modulation control signals from the button pad 104 and transmitting status information to the display screen 102 (shown in FIG. 8). As well as controlling other functions of the RC 16, which will not be described herein for purposes of brevity, the processor 114 generates a plurality of modulation parameter sets that define the amplitude, phase duration, frequency, and waveform shape in response to the user operation of the button pad 104. These new modulation parameter sets would then be transmitted to the IPG 14 via the telemetry circuitry 118, thereby adjusting the modulation parameters stored in the IPG 14 and/or programming the IPG 14. The telemetry circuitry 118 can also be used to receive modulation parameters from the CP 18. Further details of the functionality and internal componentry of the RC 16 are disclosed in U.S. Pat. No. 6,895,280, which has previously been incorporated herein by reference.

Notably, to the extent that the processor 114 is used to perform the control/processing functions of the energy consumption minimization techniques described above, the electrode sets created in response to the user entry of the pulse rate adjustment to a relatively low pulse rate to a relatively high rate can be transmitted to the IPG 14 via the telemetry circuitry 118. The energy efficient electrode set or sets selected by the processor 114 in response to the user entered pulse rate adjustment can be stored in the memory 116. For example, the electrode set(s) may be stored in the memory 116 during a fitting session performed at the clinician's office. Alternatively, the processor 114 may dynamically create the electrode set(s) as the user entry of the pulse rate is received without storing the electrode set(s) within the memory 116.

Although the foregoing programming functions have been described as being at least partially implemented in the RC 16, it should be noted that these techniques may be at least, in part, be alternatively or additionally implemented in the CP 18.

Figure 10:
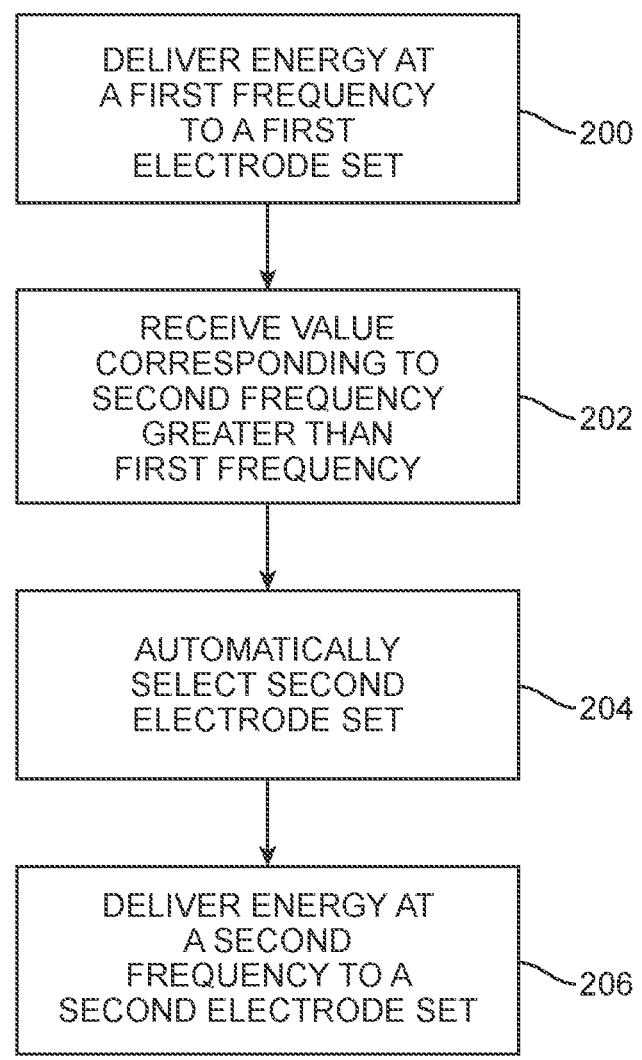
FIG. 10 is a flow diagram illustrating one technique used by the SCM system to minimize the energy consumption in the IPG of FIG. 2.

Having described the structure and function of the SCM system 10, one technique for operating the system 10 to minimize the energy consumption of the IPG 14 while providing efficacious therapy to treat an ailment, such as chronic pain, will now be described with reference to FIG. 10.

First, electrical modulation energy is delivered at a first frequency from the IPG 14 to a first set of electrodes having a first combined electrode impedance (step 200). Next, a value corresponding to a second frequency that is greater than the first frequency is received (step 202), and a second set of electrodes having a second combined electrode impedance is automatically selected in response to the user entry of the value, with the second combined electrode impedance being less than the first combined electrode impedance (step 204). As previously discussed, the second set of electrodes can be selected by adding at least one electrode to the first set of electrodes without subtracting any electrode from the first set of electrodes, or by replacing an electrode of the first set of electrodes with another electrode having an individual electrode impedance that is lower than an individual electrode impedance of the replaced electrode. Then, the electrical modulation energy is delivered at the second frequency to the second set of electrodes (step 206).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of treating an ailment of a patient using a neuromodulation device, comprising:
    delivering electrical energy at a first frequency to a first set of electrodes having a first combined electrode impedance;
    receiving a signal to switch from delivering electrical energy at the first frequency to delivering electrical energy at a second frequency greater than the first frequency;

responsive to receiving the signal to switch, automatically instructing the neuromodulation device to deliver the electrical energy at the second frequency to a second set of electrodes having a second combined electrode impedance less than the first combined electrode impedance instead of at the first frequency to the first set of electrodes; and delivering the electrical energy at a second frequency greater than the first frequency to the second set of electrodes having a second combined electrode impedance less than the first combined electrode impedance.

2. The method of claim 1, further comprising:
receiving a value corresponding to the second frequency from a user; and
automatically selecting the second set of electrodes in response to the received value.

3. The method of claim 1, wherein the first frequency is less than 1 KHz and the second frequency is equal to or greater than 1 KHz.

4. The method of claim 1, wherein the first frequency is in the range of 2 Hz-250 Hz, and the second frequency is in the range of 1 KHz-50 KHz.

5. The method of claim 1, wherein selecting the second set of electrodes includes adding at least one electrode to the first set of electrodes without subtracting any electrode from the first set of electrodes.

6. The method of claim 1, wherein selecting the second set of electrodes includes replacing an electrode of the first set of electrodes with another electrode having an individual electrode impedance that is lower than an individual electrode impedance of the replaced electrode.

7. The method of claim 1 wherein the first and second sets of electrodes are coated such that the capacitance of the first and second set of electrodes is increased.

8. A method of treating an ailment of a patient using a neuromodulation device, comprising:
delivering electrical energy at a first frequency to a first set of electrodes having a first combined electrode impedance;
receiving a signal to switch from delivering electrical energy at the first frequency to delivering electrical energy at a second frequency higher than the first frequency;
selecting a second set of electrodes having a second combined electrode impedance less than the first combined electrode impedance;
responsive to receiving the signal to switch, automatically instructing the neuromodulation device to deliver the electrical energy at the second frequency instead of at the first frequency; and
delivering the electrical energy at the second frequency to the second set of electrodes.

9. The method of claim 8, further comprising:
receiving a value corresponding to the second frequency from a user; and
automatically selecting the second set of electrodes in response to the received value.

10. The method of claim 8, wherein the first frequency is in the range of 2 Hz-250 Hz, and the second frequency is in the range of 1 KHz-50 KHz.

11. The method of claim 8, wherein an external remote controller or a clinician's programmer performs the step of selecting a second set of electrodes.

12. The method of claim 8, wherein an implantable pulse generator performs the step of selecting a second set of electrodes.

13. The method of claim 8, wherein selecting a second set of electrodes includes adding an electrode.

14. The method of claim 8, wherein selecting a second set of electrodes includes replacing an electrode of the first set of electrodes with another electrode having an individual electrode impedance that is lower than an individual electrode impedance of the replaced electrode.

15. The method of claim 8, wherein the first frequency is less than 1 kHz and the second frequency is greater than 1 kHz.

16. A method of treating an ailment of a patient using a neuromodulation device, comprising:
delivering electrical energy at a first frequency of less than 1 kHz to a first set of electrodes having a first combined electrode impedance;
receiving a signal to switch from delivering electrical energy at the first frequency to delivering electrical energy at a second frequency greater than or equal to 1 KHz;
selecting a second set of electrodes having a second combined electrode impedance less than the first combined electrode impedance;
automatically replacing an electrode of the first set of electrodes with another electrode having an individual electrode impedance that is lower than an individual electrode impedance of the replaced electrode to provide the second set of electrodes;
responsive to receiving the signal to switch, automatically instructing the neuromodulation device to deliver the electrical energy at the second frequency to the second set of electrodes instead of at the first frequency to the first set of electrodes; and
delivering the electrical energy at the second frequency to the second set of electrodes.

17. The method of claim 16, further comprising:
receiving a value corresponding to the second frequency from a user; and
automatically selecting the second set of electrodes in response to the received value.

18. The method of claim 16, wherein the first frequency is in the range of 2 Hz-250 Hz, and the second frequency is in the range of 1 KHz-50 KHz.

19. The method of claim 16, wherein the ailment is chronic pain.

20. The method of claim 16, wherein the electrodes are implanted within the patient.

* * * * *